United States Patent
Vitek et al.

(10) Patent No.: US 9,852,727 B2
(45) Date of Patent: Dec. 26, 2017

(54) MULTI-SEGMENT ULTRASOUND TRANSDUCERS

(75) Inventors: Shuki Vitek, Haifa (IL); Yoni Hertzberg, Givataim (IL); Yoav Medan, Haifa (IL)

(73) Assignee: INSIGHTEC, LTD., Tirat Carmel (IL)

(*) Notice: Subject to any disclaimer, the term of this patent is extended or adjusted under 35 U.S.C. 154(b) by 1140 days.

(21) Appl. No.: 12/769,072

(22) Filed: Apr. 28, 2010

(65) Prior Publication Data

US 2011/0270075 A1    Nov. 3, 2011

(51) Int. Cl.
| | |
|---|---|
| A61H 1/00 | (2006.01) |
| G10K 11/35 | (2006.01) |
| A61N 7/02 | (2006.01) |
| G10K 11/34 | (2006.01) |
| A61N 7/00 | (2006.01) |
| A61B 90/00 | (2016.01) |

(52) U.S. Cl.
CPC ............. *G10K 11/352* (2013.01); *A61N 7/02* (2013.01); *G10K 11/346* (2013.01); *A61B 2090/374* (2016.02); *A61N 2007/0065* (2013.01); *A61N 2007/0078* (2013.01); *A61N 2007/0091* (2013.01); *A61N 2007/0095* (2013.01)

(58) Field of Classification Search
CPC ......... A61N 7/00; A61N 7/02; A61H 23/0245
USPC .......................................................... 601/2
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,559,159 A | 1/1971 | Harms et al. |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,052,723 A | 10/1977 | Miller |
| 4,074,564 A | 2/1978 | Anderson |
| 4,206,653 A | 6/1980 | Lemay |
| 4,211,132 A | 7/1980 | Nichols, III et al. |
| 4,221,132 A | 9/1980 | Poole |
| 4,307,613 A | 12/1981 | Fox |
| 4,339,952 A | 7/1982 | Foster |
| 4,441,486 A | 4/1984 | Pounds |
| 4,454,597 A | 6/1984 | Sullivan |
| 4,478,083 A | 10/1984 | Hassler et al. |
| 4,505,156 A | 3/1985 | Questo |

(Continued)

FOREIGN PATENT DOCUMENTS

| | | |
|---|---|---|
| CN | 1744861 A | 3/2006 |
| CN | 1981708 A | 6/2007 |

(Continued)

OTHER PUBLICATIONS

Fronheiser et al., "3D Acoustic Radiation Force Impulse (ARFI) Imaging Using a 2D Matrix Array: Feasibility Study," Ultrasonics Symposium, pp. 1144-1147 (Oct. 2006).

(Continued)

*Primary Examiner* — Tse Chen
*Assistant Examiner* — Hien Nguyen
(74) *Attorney, Agent, or Firm* — Morgan, Lewis & Bockius LLP

(57) ABSTRACT

Disclosed are systems and methods for focusing ultrasound transducers that include multiple separate, independently movable transducer segments.

20 Claims, 5 Drawing Sheets

(56) References Cited

U.S. PATENT DOCUMENTS

| | | | |
|---|---|---|---|
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,586,512 A | 5/1986 | Do-huu et al. |
| 4,616,231 A | 10/1986 | Autrey et al. |
| 4,636,964 A | 1/1987 | Jacobs et al. |
| 4,646,756 A | 3/1987 | Watmough et al. |
| 4,647,808 A | 3/1987 | Shibuya |
| 4,662,222 A | 5/1987 | Johnson |
| 4,757,820 A | 7/1988 | Itoh |
| 4,817,614 A | 4/1989 | Hassler et al. |
| 4,823,053 A | 4/1989 | Mccracken et al. |
| 4,858,597 A | 8/1989 | Kurtze et al. |
| 4,858,613 A | 8/1989 | Fry et al. |
| 4,865,042 A | 9/1989 | Umemura et al. |
| 4,886,491 A | 12/1989 | Parisi et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 4,938,217 A | 7/1990 | Lele |
| 4,957,099 A | 9/1990 | Hassler |
| 5,015,929 A | 5/1991 | Cathignol et al. |
| 5,143,063 A | 9/1992 | Fellner |
| 5,165,412 A | 11/1992 | Okazaki |
| 5,172,343 A | 12/1992 | O'donnell |
| 5,197,475 A | 3/1993 | Antich et al. |
| 5,209,221 A | 5/1993 | Riedlinger |
| 5,211,160 A | 5/1993 | Talish et al. |
| 5,247,935 A | 9/1993 | Cline et al. |
| 5,266,863 A | 11/1993 | Nonami et al. |
| 5,267,221 A | 11/1993 | Miller et al. |
| 5,269,307 A | 12/1993 | Fife et al. |
| 5,271,400 A | 12/1993 | Dumoulin et al. |
| 5,275,165 A | 1/1994 | Ettinger et al. |
| 5,291,890 A | 3/1994 | Cline et al. |
| 5,305,737 A | 4/1994 | Vago |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,388,461 A | 2/1995 | Rigby |
| 5,391,140 A | 2/1995 | Schaetzle et al. |
| 5,413,550 A | 5/1995 | Castel |
| 5,419,761 A | 5/1995 | Narayanan et al. |
| 5,435,312 A | 7/1995 | Spivey et al. |
| 5,443,068 A | 8/1995 | Cline et al. |
| 5,474,071 A | 12/1995 | Chapelon et al. |
| 5,477,736 A | 12/1995 | Lorraine |
| 5,485,839 A | 1/1996 | Aida et al. |
| 5,490,512 A | 2/1996 | Kwon et al. |
| 5,490,840 A | 2/1996 | Uzgiris et al. |
| 5,507,790 A | 4/1996 | Weiss |
| 5,514,086 A | 5/1996 | Parisi et al. |
| 5,520,186 A | 5/1996 | Deitrich |
| 5,520,188 A | 5/1996 | Hennige et al. |
| 5,520,612 A | 5/1996 | Winder et al. |
| 5,526,814 A | 6/1996 | Cline et al. |
| 5,527,273 A | 6/1996 | Manna et al. |
| 5,546,360 A | 8/1996 | Deegan |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,606,971 A | 3/1997 | Sarvazyan |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,718,226 A | 2/1998 | Riza |
| 5,722,411 A | 3/1998 | Suzuki et al. |
| 5,725,482 A | 3/1998 | Bishop |
| 5,728,062 A | 3/1998 | Brisken |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,769,879 A | 6/1998 | Richards et al. |
| 5,784,336 A * | 7/1998 | Gopinathan et al. ......... 367/123 |
| 5,810,008 A | 9/1998 | Dekel et al. |
| 5,810,731 A | 9/1998 | Sarvazyan et al. |
| 5,817,021 A | 10/1998 | Reichenberger |
| 5,817,036 A | 10/1998 | Anthony et al. |
| 5,823,990 A | 10/1998 | Henley |
| 5,827,204 A | 10/1998 | Grandia et al. |
| 5,873,845 A | 2/1999 | Cline et al. |
| 5,884,631 A | 3/1999 | Silberg |
| 5,885,211 A | 3/1999 | Eppstein et al. |
| 5,891,040 A | 4/1999 | Grenon et al. |
| 5,897,495 A | 4/1999 | Aida et al. |
| 5,904,659 A | 5/1999 | Duarte et al. |
| 5,922,962 A | 7/1999 | Ishrak et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A * | 11/1999 | Ishibashi et al. ................ 601/2 |
| 6,004,269 A | 12/1999 | Crowley et al. |
| 6,007,499 A | 12/1999 | Martin et al. |
| 6,013,048 A | 1/2000 | Podany et al. |
| 6,023,636 A | 2/2000 | Wendt et al. |
| 6,032,675 A | 3/2000 | Rubinsky |
| 6,033,375 A | 3/2000 | Brumbach |
| 6,036,644 A | 3/2000 | Schutt |
| 6,039,048 A | 3/2000 | Silberg |
| 6,042,556 A | 3/2000 | Beach et al. |
| 6,045,777 A | 4/2000 | Church et al. |
| 6,071,239 A | 6/2000 | Cribbs et al. |
| 6,088,295 A | 7/2000 | Altes |
| 6,106,511 A | 8/2000 | Jensen |
| 6,113,558 A | 9/2000 | Rosenschein et al. |
| 6,113,559 A | 9/2000 | Klopotek |
| 6,128,522 A | 10/2000 | Acker et al. |
| 6,128,958 A | 10/2000 | Cain |
| 6,135,960 A | 10/2000 | Holmberg |
| 6,135,971 A | 10/2000 | Hutchinson et al. |
| 6,142,939 A | 11/2000 | Eppstein et al. |
| 6,156,549 A | 12/2000 | Drewes et al. |
| 6,193,659 B1 | 2/2001 | Ramamurthy et al. |
| 6,217,530 B1 | 4/2001 | Martin et al. |
| 6,242,915 B1 | 6/2001 | Hurd |
| 6,246,895 B1 * | 6/2001 | Plewes ......................... 600/410 |
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,350,245 B1 | 2/2002 | Cimino |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |

(56) References Cited

U.S. PATENT DOCUMENTS

| | | |
|---|---|---|
| 6,424,597 B1 | 7/2002 | Bolomey et al. |
| 6,425,867 B1 | 7/2002 | Vaezy et al. |
| 6,428,477 B1 | 8/2002 | Mason |
| 6,428,532 B1 | 8/2002 | Doukas et al. |
| 6,433,464 B2 | 8/2002 | Jones |
| 6,461,314 B1 | 10/2002 | Pant et al. |
| 6,475,150 B2 | 11/2002 | Haddad |
| 6,478,739 B1 | 11/2002 | Hong |
| 6,503,204 B1 | 1/2003 | Sumanaweera et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,064 B1 | 1/2003 | Phinney et al. |
| 6,511,428 B1 | 1/2003 | Azuma et al. |
| 6,522,142 B1 | 2/2003 | Freundlich |
| 6,523,272 B1 | 2/2003 | Morales |
| 6,524,251 B2 | 2/2003 | Rabiner et al. |
| 6,543,272 B1 | 4/2003 | Vitek |
| 6,554,826 B1 | 4/2003 | Deardorff |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,589,174 B1 | 7/2003 | Chopra et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 * | 9/2003 | Friedman et al. ............ 601/2 |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,676,602 B1 | 1/2004 | Barnes et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,805,129 B1 | 10/2004 | Pless et al. |
| 6,824,516 B2 | 11/2004 | Batten et al. |
| 6,936,046 B2 | 8/2005 | Hissong et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,429,248 B1 | 9/2008 | Winder et al. |
| 7,452,357 B2 | 11/2008 | Vlegele et al. |
| 7,505,805 B2 | 3/2009 | Kuroda |
| 7,505,808 B2 | 3/2009 | Anderson et al. |
| 7,507,213 B2 | 3/2009 | Schultheiss et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 7,819,805 B2 | 10/2010 | Davies et al. |
| 8,002,706 B2 | 8/2011 | Vortman et al. |
| 8,057,408 B2 | 11/2011 | Cain et al. |
| 8,075,488 B2 | 12/2011 | Burton |
| 8,088,067 B2 | 1/2012 | Vortman et al. |
| 8,409,099 B2 | 4/2013 | Vitek et al. |
| 8,425,424 B2 | 4/2013 | Zadicario et al. |
| 8,608,672 B2 | 12/2013 | Vortman et al. |
| 8,617,073 B2 | 12/2013 | Prus et al. |
| 8,661,873 B2 | 3/2014 | Medan et al. |
| 2001/0031922 A1 | 10/2001 | Weng et al. |
| 2002/0016557 A1 | 2/2002 | Duarte et al. |
| 2002/0035779 A1 | 3/2002 | Krieg et al. |
| 2002/0082528 A1 | 6/2002 | Friedman et al. |
| 2002/0082589 A1 | 6/2002 | Friedman et al. |
| 2002/0095087 A1 | 7/2002 | Mourad et al. |
| 2002/0111552 A1 | 8/2002 | Maor et al. |
| 2002/0151790 A1 | 10/2002 | Abend |
| 2002/0161300 A1 | 10/2002 | Hoff et al. |
| 2002/0188229 A1 | 12/2002 | Ryaby |
| 2003/0004439 A1 | 1/2003 | Pant et al. |
| 2003/0060820 A1 | 3/2003 | Maguire et al. |
| 2003/0187371 A1 | 10/2003 | Vortman et al. |
| 2004/0030251 A1 | 2/2004 | Ebbini et al. |
| 2004/0059265 A1 | 3/2004 | Candy et al. |
| 2004/0068186 A1 | 4/2004 | Ishida et al. |
| 2004/0082868 A1 | 4/2004 | Campbell et al. |
| 2004/0116809 A1 | 6/2004 | Chow et al. |
| 2004/0122316 A1 | 6/2004 | Satoh |
| 2004/0122323 A1 | 6/2004 | Vortman et al. |
| 2004/0143187 A1 | 7/2004 | Biagi et al. |
| 2004/0147919 A1 | 7/2004 | Behl et al. |
| 2004/0210134 A1 | 10/2004 | Hynynen et al. |
| 2004/0210135 A1 | 10/2004 | Hynynen et al. |
| 2004/0236253 A1 | 11/2004 | Vortman et al. |
| 2004/0236523 A1 | 11/2004 | Taylor |
| 2004/0267126 A1 | 12/2004 | Takeuchi |
| 2005/0033201 A1 | 2/2005 | Takahashi et al. |
| 2005/0096542 A1 | 5/2005 | Weng et al. |
| 2005/0131301 A1 | 6/2005 | Peszynski et al. |
| 2005/0154304 A1 | 7/2005 | Robinson |
| 2005/0199058 A1 | 9/2005 | Danz et al. |
| 2005/0203444 A1 | 9/2005 | Schonenberger et al. |
| 2005/0240126 A1 | 10/2005 | Foley et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0052706 A1 | 3/2006 | Hynynen et al. |
| 2006/0058671 A1 * | 3/2006 | Vitek et al. ............ 600/447 |
| 2006/0058678 A1 | 3/2006 | Vitek et al. |
| 2006/0106300 A1 | 5/2006 | Seppenwoolde et al. |
| 2006/0173307 A1 | 8/2006 | Amara et al. |
| 2006/0173321 A1 | 8/2006 | Kubota et al. |
| 2006/0173385 A1 | 8/2006 | Lidgren et al. |
| 2006/0184034 A1 | 8/2006 | Haim et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2006/0235302 A1 | 10/2006 | Grossman et al. |
| 2007/0016039 A1 | 1/2007 | Vortman et al. |
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0167798 A1 | 7/2007 | Cai et al. |
| 2007/0197918 A1 | 8/2007 | Vitek et al. |
| 2007/0219470 A1 | 9/2007 | Talish et al. |
| 2007/0239062 A1 | 10/2007 | Chopra et al. |
| 2007/0265560 A1 | 11/2007 | Soltani et al. |
| 2007/0276237 A1 | 11/2007 | Li |
| 2008/0027342 A1 | 1/2008 | Rouw et al. |
| 2008/0030104 A1 | 2/2008 | Prus |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0103558 A1 | 5/2008 | Wenzel et al. |

(56) References Cited

U.S. PATENT DOCUMENTS

| | | | |
|---|---|---|---|
| 2008/0108900 A1 | 5/2008 | Lee et al. |
| 2008/0125660 A1 | 5/2008 | Yao et al. |
| 2008/0183077 A1 | 7/2008 | Moreau-Gobard et al. |
| 2008/0228081 A1 | 9/2008 | Becker et al. |
| 2008/0312562 A1 | 12/2008 | Routh et al. |
| 2009/0088623 A1 | 4/2009 | Vortman et al. |
| 2009/0093721 A1 | 4/2009 | Katsuyama |
| 2009/0096450 A1 | 4/2009 | Roland |
| 2009/0118619 A1 | 5/2009 | Oshiki |
| 2010/0030076 A1 | 2/2010 | Vortman et al. |
| 2010/0056962 A1 | 3/2010 | Vortman et al. |
| 2010/0125193 A1 | 5/2010 | Zadicario |
| 2010/0179425 A1 | 7/2010 | Zadicario |
| 2010/0268088 A1 | 10/2010 | Prus et al. |
| 2010/0274130 A1 | 10/2010 | Anand et al. |
| 2010/0318002 A1 | 12/2010 | Prus et al. |
| 2011/0066032 A1 | 3/2011 | Vitek et al. |
| 2011/0094288 A1 | 4/2011 | Medan et al. |
| 2011/0130663 A1 | 6/2011 | Raju et al. |
| 2011/0137147 A1 | 6/2011 | Skliar et al. |
| 2011/0251527 A1* | 10/2011 | Kushculey et al. ............... 601/2 |
| 2011/0270136 A1 | 11/2011 | Vitek et al. |
| 2012/0083695 A1 | 4/2012 | Napolitano et al. |
| 2013/0077441 A1 | 3/2013 | Ramamurthy et al. |
| 2014/0112095 A1 | 4/2014 | Medan et al. |

FOREIGN PATENT DOCUMENTS

| | | |
|---|---|---|
| DE | 4345308 C2 | 2/2001 |
| DE | 10102317 A1 | 8/2002 |
| EP | 0031614 A1 | 7/1981 |
| EP | 151073 A2 | 8/1985 |
| EP | 174920 A1 | 3/1986 |
| EP | 272347 A1 | 6/1988 |
| EP | 0320303 | 6/1989 |
| EP | 450334 A2 | 10/1991 |
| EP | 462311 A1 | 12/1991 |
| EP | 467690 A2 | 1/1992 |
| EP | 0558029 | 9/1993 |
| EP | 627206 A2 | 12/1994 |
| EP | 734742 A2 | 10/1996 |
| EP | 1132054 | 9/2001 |
| EP | 1582886 A1 | 10/2005 |
| EP | 1591073 | 11/2005 |
| EP | 1774920 A1 | 4/2007 |
| EP | 1790384 | 5/2007 |
| EP | 1936404 | 6/2008 |
| FR | 2692999 A1 | 12/1993 |
| FR | 2806611 A1 | 9/2001 |
| GB | 2019565 A | 10/1979 |
| JP | 5-92008 | 4/1993 |
| JP | 7-184907 | 7/1995 |
| JP | 7-231895 | 9/1995 |
| JP | 7-313518 | 12/1995 |
| JP | 11313833 A | 11/1999 |
| JP | 00/166940 | 6/2000 |
| JP | 01/516075 | 9/2001 |
| JP | 02/530145 | 9/2002 |
| JP | 2006-503653 T | 2/2006 |
| WO | WO-9100059 A1 | 1/1991 |
| WO | 91/15999 A1 | 10/1991 |
| WO | 91/19332 A1 | 12/1991 |
| WO | 93/15415 A1 | 8/1993 |
| WO | WO-95/014505 | 6/1995 |
| WO | 97/17018 A1 | 5/1997 |
| WO | WO-9852465 A1 | 11/1998 |
| WO | WO-0031614 A1 | 6/2000 |
| WO | 00/78232 A1 | 12/2000 |
| WO | 01/43640 A2 | 6/2001 |
| WO | 01/59337 A3 | 8/2001 |
| WO | WO-01/58337 | 8/2001 |
| WO | WO-0166189 A1 | 9/2001 |
| WO | 01/80708 A2 | 11/2001 |
| WO | WO-0180709 A2 | 11/2001 |
| WO | 01/80708 A3 | 3/2002 |
| WO | WO-02/43805 | 6/2002 |
| WO | WO-02/44753 | 6/2002 |
| WO | WO-0258791 A1 | 8/2002 |
| WO | WO-03/013654 A1 | 2/2003 |
| WO | 03/070105 A1 | 8/2003 |
| WO | WO-03/097162 A2 | 11/2003 |
| WO | WO-03/098232 A2 | 11/2003 |
| WO | 2004/021044 A1 | 3/2004 |
| WO | 2004/066856 A1 | 8/2004 |
| WO | WO-2004/093686 | 11/2004 |
| WO | 2005/038745 A1 | 4/2005 |
| WO | WO-200558029 A2 | 6/2005 |
| WO | WO-2006018837 A2 | 2/2006 |
| WO | WO-2006/021851 | 3/2006 |
| WO | WO-2006025001 A1 | 3/2006 |
| WO | WO-2006087649 A1 | 8/2006 |
| WO | WO-2006/119572 | 11/2006 |
| WO | WO-2007/051066 | 5/2007 |
| WO | WO-2007073551 A1 | 6/2007 |
| WO | 2007/093998 A1 | 8/2007 |
| WO | 2008/015523 A2 | 2/2008 |
| WO | WO-2008/039449 | 4/2008 |
| WO | WO-2008050278 A1 | 5/2008 |
| WO | WO-200875203 A2 | 6/2008 |
| WO | WO-2008119054 A1 | 10/2008 |
| WO | WO-2009055587 A1 | 4/2009 |
| WO | 2009/085466 A1 | 7/2009 |
| WO | WO-2009/081339 | 7/2009 |
| WO | WO-2009/094554 | 7/2009 |
| WO | WO-2010/058292 | 5/2010 |
| WO | WO-2010/082135 | 7/2010 |
| WO | WO-2010/119340 | 10/2010 |
| WO | WO-2010/143072 | 12/2010 |
| WO | WO-2011/013001 | 2/2011 |
| WO | WO-2011/024074 | 3/2011 |
| WO | WO-2011/045669 | 4/2011 |

OTHER PUBLICATIONS

Wu et al., "MRImaging of Shear Waves Generated by Focused Ultrasound," Magnetic Resonance in Medicine, vol. 43, pp. 111-115 (2000).

Heikkila et al., "Simulations of Lesion Detection Using a Combined Phased Array LHMI-Technique,"Ultrasonics, IPC Science and Technology Press Ltd., vol. 48, No. 6-7, pp. 568-573 (Nov. 2008).

International Search Report and Written Opinion dated Dec. 19, 2011 for International Application No. PCT/IB2011/001293 (13 pages).

McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

Botros et al., "A hybrid computational model for ultrasound phased-array heating in presence of strongly scattering obstacles," IEEE Trans. on Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. on Microwave Theory & Techniques, vol. MTT-34, No. 5, pp. 542-551 (May 1986).

Chen et al., "MR Acoustic Radiation Force Imaging: Comparison of Encoding Gradients."

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

(56) References Cited

OTHER PUBLICATIONS

Fjield et al, "The Combined Concentric-ring and Sector-vortex Phased Array for MRI Guided Ultrasound Surgery," IEEE Trans. on Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. on Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
International Preliminary Report on Patentability in International Patent Application No. PCT/IB2004/001512, dated Dec. 8, 2005.
International Search Report and Written Opinion in International Patent Application No. PCT/IB2004/001498, dated Aug. 31, 2004.
International Search Report and Written Opinion in International Patent Application No. PCT/IB2005/002273, dated Dec. 20, 2005.
International Search Report and Written Opinion in International Patent Application No. PCT/IB2005/002413, dated Nov. 22, 2005.
International Search Report and Written Opinion in International Patent Application No. PCT/IB2006/001641, dated Sep. 25, 2006.
International Search Report and Written Opinion in International Patent Application No. PCT/IB2006/003300, dated Feb. 14, 2008.
International Search Report and Written Opinion in International Patent Application No. PCT/IB2007/001079, dated Dec. 10, 2007.
International Search Report and Written Opinion in International Patent Application No. PCT/IB2007/002134, dated Dec. 13, 2007.
International Search Report and Written Opinion in International Patent Application No. PCT/IB2007/002140, dated Dec. 29, 2008.
International Search Report and Written Opinion in International Patent Application No. PCT/IB2008/003069, dated Apr. 27, 2009.
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. on Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. on Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. on Therapeutic Ultrasound, edited by E.S. Ebbini, U. of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, dated Feb. 24, 2003.
Written Opinion in International Patent Application No. PCT/IL02/00477, dated Feb. 25, 2003.
Written Opinion in International Patent Application No. PCT/IB03/05551, dated Sep. 10, 2004.
"How is Ablatherm treatment performed?" http://www.edap-hifu.com/eng/physicians/hifu/3c_treatment_treat-description.htm, accessed Jan. 3, 2003.

"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
International Search Report and Written Opinion in International Patent Application No. PCT/IB2010/000189, dated Jun. 1, 2010.
International Search Report for PCT/IB03/05551 dated Mar. 2, 2004 (5 pages).
International Search Report and Written Opinion in Internation Patent Application No. PCT/IB2010/000971, dated Jul. 29, 2010 (9 pages).
McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).
Suprijanto et al. "Displacement Correction Scheme for MR-Guided Interstitial Laser Therapy," Ellis RE, Peters TM (Eds.): MiCCAI, LNCS 2879, pp. 399-407 (2003).
Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).
De Senneville et al., "An Optimised Multi-Baseline Approach for On-Line MR-Temperature Monitoring on Commodity Graphics Hardware," Biomedical Imaging, pp. 1513-1516 (2008).
Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).
"Body Sculpting/Liposuction", available online at<http://www.cosmeticdoctor.com/sculpting.htm>, retrieved on Mar. 17, 2000, pp. 1-3.
"For Ultrasonic Liposuction", available online at <http://www.ultrasonic-liposuction.com/index.html>, retrieved on Mar. 17, 2000, 1 page.
"Glossary", available online at <http://www.lipoinfo.com/glossary.htm>, retrieved on Mar. 17, 2000, pp. 1-14.
"Internal, External Ultrasound Aids Liposuction", available online at<http://surgery.medscape.com/IMNG/SkinAllergyNews/1998/v.29.n03/san2903.46. 01.html> retrieved on Mar. 17, 2000, pp. 1-3.
"Liposuction", available online at <http://www.swmed.edu/home.sub.-pages/library/consumer/liposuc.htm>, retrieved on Mar. 17, 2000, 1 page.
"The Lipo Symposium", available online at <http://liposymposium.com/details/History/>, retrieved on Mar. 17, 2000, 1 page.
"Trends in Cosmetic Surgery: Lipoplasty (Liposuction)", available online at <http://www.wrc-gbmc.org/4rd.html>, retrieved on Mar. 17, 2000, 1 page.
"Ultrasonic Liposuction; Body Contouring", available online at <http://www.drloomis.com/serv01.htm,>, retrieved on Mar. 17, 2000, pp. 1-2.
"Ultrasonic-Assisted Liposuction", available online at <http://www.liposymposium.com/details/procedure/techniqus/UAL/>, retrieved on Mar. 17, 2000, pp. 1-2.
"Ultrasound Assisted Lipoplasty", available online at <http://www.plasticsurgery.org/surgery/ual.htm>, retrieved on Mar. 17, 2000, pp. 1-4.
"Ultrasound-Assisted Liposuction", available online at <http://www.drhobar.com/ual.htm>, retrieved on Mar. 17, 2000, pp. 1-4.

(56) References Cited

OTHER PUBLICATIONS

"Ultrasound Liposuction or Ultrasound Assisted Lipoplasty—UAL", available online at <http://www.ultrasonic-liposuction.com/InformationD.html>, retrieved on Mar. 17, 2000, pp. 1-2.

"Ultrasound-Assisted Liposuction", available online at <http://www.providence-hospital.org/technology/lipo.htm>, retrieved on Mar. 17, 2000, 1 page.

"External Ultrasonic Liposuction", available online at <http://www.lipoinfo.com/chap14..htm.>, retrived on Mar. 17, 2000.

"Liquefying the Fat: Ultrasound Expands Score of Liposuction", available online at <http://www.swmed.edu/home.sub.-pages/new/liquilip.htm>, retrieved on Mar. 17, 2000, pp. 1-2.

International Application Serial No. PCT/IB2004/001512, International Search Report and Written Opinion dated Sep. 7, 2004, 7 pages.

International Application Serial No. PCT/IB2010/002757, International Preliminary Report on Patentability dated Apr. 17, 2012, 10 pages.

International Application Serial No. PCT/IB2010/002757, International Search Report and Written Opinion dated Sep. 7, 2011, 15 pages.

International Application Serial No. PCT/IB2010/002265, International Search Report and Written Opinion dated Jun. 22, 2011, 16 pages.

International Application Serial No. PCT/IB2010/002265, Partial International Search Report dated Mar. 11, 2011, 4 pages.

International Application Serial No. PCT/IB2011/001293, International Preliminary Report on Patentability dated Nov. 8, 2012, 9 pages.

International Application Serial No. PCT/IB2011/001375, International Search Report and Written Opinion dated Nov. 10, 2011, 12 pages.

International Application Serial No. PCT/IB2011/001375, International Preliminary Report on Patentability dated Nov. 8, 2012, 9 pages.

Examination Report in Chinese Patent Application No. 200680029730.8, dated Apr. 29, 2010, 7 pages.

Examination Report in Japanese Patent Application No. 2011-536968, dated Oct. 21, 2013, 18 pages.

Examination Report in Chinese Patent Application No. 200980153997.1, dated Apr. 15, 2014, 18 pages.

Examination Report in Chinese Patent Application No. 201080011633.2, dated Oct. 8, 2013, 19 pages.

Bates, B, "External Ultrasound's Liposuction Role Debated", Available Online at <http://molecularmedicine.medscape.com/IMNG/SkinAllergyNews/19 . . . /san3003. 06.02.htm>, retrieved on Mar. 17, 2000, pp. 1-2.

Daum et al., "Thermal Dose Optimization Via Temporal Switching in Ultrasound Surgery", IEEE Transactions on Ultrasonics, Ferroelectrics, and Frequency Control, vol. 45, No. 1, Jan. 1998, pp. 208-215.

Eisenhauer, K, "6/24—Ultrasound Liposuction", available online at <http://www.channel6000.com/health/health-990624-191707.html>, retrieved on Mar. 17, 2000, pp. 1-2.

Fjield et al., "Low-Profile Lenses for Ultrasound Surgery", Physics in Medicine and Biology, vol. 44, No. 7, Jul. 1999, pp. 1803-1813.

Hynynen et al., "Principles of MR-Guided Focused Ultrasound", Chapter 25, pp. 237-243.

LIPOINFO.COM, "Glossary 70 words", available online at <http://www.lipoinfo.com/glossary.htm>, retrieved on Mar. 17, 2000, pp. 1-14.

Nigro, D M., "Ultrasound Assisted Lipoplasty (Liposuction)", available online at <http://www.drnigro.com/dennis.htm,>, retrieved on Mar. 17, 2000, 1 page.

* cited by examiner

US 9,852,727 B2

MULTI-SEGMENT ULTRASOUND TRANSDUCERS

FIELD OF THE INVENTION

The present invention relates, generally, to systems and methods for ultrasound focusing. In particular, various embodiments are directed to focusing a multi-segment ultrasound transducer array utilizing, for example, magnetic-resonance acoustic radiation force imaging (MR-ARFI).

BACKGROUND

Focused ultrasound (i.e., acoustic waves having a frequency greater than about 20 kilohertz) can be used to image or therapeutically treat internal body tissues within a patient. For example, ultrasonic waves may be used to ablate tumors, eliminating the need for the patient to undergo invasive surgery. For this purpose, a piezo-ceramic transducer is placed externally to the patient, but in close proximity to the tissue to be ablated ("the target"). The transducer converts an electronic drive signal into mechanical vibrations, resulting in the emission of acoustic waves. The transducer may be shaped so that the waves converge in a focal zone. Alternatively or additionally, the transducer may be formed of a plurality of individually driven transducer elements whose phases can each be controlled independently from one another and, thus, can be set so as to result in constructive interference of the individual acoustic waves in the focal zone. Such a "phased-array" transducer facilitates steering the focal zone to different locations by adjusting the relative phases between the transducers. Magnetic resonance imaging (MRI) may be utilized to visualize the focus and target in order to guide the ultrasound beam.

To minimize, for a given focus intensity, the intensity experienced by tissue regions surrounding the target, the ultrasound waves preferably come from multiple directions. This may require large transducer surfaces that surround the target as much as possible. Large-area transducers arrays may, however, be difficult to handle, and may complicate beam steering. Moreover, the placement of the transducer may be constrained by anatomical barriers, depending on the particular target location inside the body. For the treatment of different tissues and organs, differently shaped transducers may be desirable. Further, even if the location of the transducer with respect to the target is geometrically optimal, ultrasound waves coming from certain regions of the transducer surface may be blocked by strongly absorbing tissue, such as, e.g., bone, or other internal anatomical barriers. Accordingly, there is a need for focused ultrasound transducer arrays that are adjustable to various anatomical constraints.

SUMMARY

The present invention provides, in various embodiments, ultrasound transducer arrangements including a plurality of separate, independently movable segments, and systems and methods for calibrating and driving these segments collectively to generate a common, "global" focus. The segments may be placed around a target in a way that exploits acoustic windows, i.e., beam paths along which the acoustic waves can travel without undergoing significant absorption, reflection, or scattering. In some embodiments, the transducer segments are mechanically coupled, either loosely or strongly, which reduces the number of degrees of freedom of the relative motion. In other embodiments, the segments are mechanically uncoupled.

In typical embodiments, each segment contains a plurality (e.g., tens, hundreds, or thousands of) transducer elements. In operation, the relative phases and/or amplitudes of these elements may be adjusted to steer the ultrasound beam emanating from the respective transducer segment along a desired direction, and create a focus at a desired distance. The required relative phases and/or amplitudes may be computed from information about the geometry of the transducer segment, its location and orientation relative to the target, and relevant material properties (e.g., the speed of sound at the employed frequency) along the beam path (hereinafter collectively referred to as a "sonication model"). Alternatively, they may be determined experimentally, either in the treatment setup itself or in a calibration setup before integration of the segment into the transducer arrangement for treatment, through iterative measurements of the focus quality and phase/amplitude adjustments. In some embodiments, computations based on a sonciation model are advantageously combined with experimental feedback.

Once the segments have been individually focused (so that the outputs of their transducer elements converge at a common location), their respective foci may be brought to overlap. In some embodiments, focusing the individual beams at the target location may suffice to generate the desired global focus. In general, however, the individual foci will be at least slightly displaced from one another, resulting in a blurred global focus. To improve the focus quality, one or more segments may be physically moved to translate and/or rotate the beam, and/or phase shift gradients may be applied across the transducer elements to adjust the beam steering angle(s).

In addition to the co-location of the foci of the various transducer segments, a global focus generally requires that the various acoustic waves arrive (at least approximately) in phase at the center of the global focus. The total phase of an acoustic wave from an individual segment may be adjusted by shifting the phases of all its elements simultaneously by the same amount. The acoustic waves from the different transducer segments may be brought in phase by varying the total phase associated with one segment while keeping the total phases of the other segments constant, and observing the resulting variation in the focus intensity and quality. The phase difference between the variable and constant phases at which the focus intensity in the center is maximized corresponds to the amount by which the total phase of the segment under test should be adjusted to improve the global focus. This procedure may be carried out for all of the segments in turn to achieve constructive interference at the center of the global focus. To reduce the number of sonications needed for this adjustment procedure, the initial settings of the relative total phases of the transducer segments may be based on information, to the extent available, about the relative locations and orientations of the segments.

Various techniques, including, for example, thermal imaging and MR-ARFI, may be used to visualize the focus during the calibration procedure described above. Thermal imaging is not possible in all types of tissues; for instance, it does not work in fat tissue because the resonant frequency of fat tissue is largely independent of temperature in a temperature range suitable for imaging Also, thermal imaging is associated with a local rise in temperature that is desirably avoided in certain tissue types, e.g., in a blood clot, for medical reasons. Magnetic-resonance acoustic radiation force imaging, on the other hand, is applicable to all types of soft tissue. It involves magnetic resonance imaging (MRI) of minute material displacements resulting from pressure associated with an acoustic wave. The displacement increases with the acoustic field intensity. Thus, by adjusting the locations, beam directions, and/or total phases of the transducer segments to increase the material displacement, the intensity at the focus and, consequently, the focus quality may be improved. Compared with thermal imaging, MR-ARFI provides sufficient signal strength and contrast at lower levels of energy deposited into the material. Therefore, MR-ARFI may be employed in many situations in which thermal imaging, due to its potential to damage tissue, would be precluded. Further, MR-ARFI may allow a greater number of measurements, and hence a better focus, before the accumulated energy deposit reaches the limit of what is physiologically tolerable.

In one aspect, various embodiments of the invention are directed to a method of focusing an ultrasound transducer arrangement including a plurality of separate, independently movable segments, in which each transducer segment, in turn, includes a plurality of transducer elements. The transducer segments may be mechanically uncoupled or mechanically coupled. Mechanical coupling between two or more segments may eliminate a degree of freedom of relative motion between the segments. The method includes performing the following steps for each of the plurality of transducer segments: (i) driving the segment so as to generate an ultrasound focus; (ii) measuring a total phase associated with the focus relative to a phase of a global focus; and (iii) determining whether the focus is in phase with the global focus and, if not, adjusting the total phase of the focus to a phase of the global focus.

Driving the segment may include setting relative phases between the transducer elements of that segment so as to generate the ultrasound focus. The relative phase settings may be based (at least in part) on a sonication model. Alternatively, the relative phase settings may be determined (at least in part) by (i) driving a selected element of the segment at a variable phase while driving the other elements at a constant phase, thereby varying an intensity of the focus; (ii) determining a phase difference, if any, between the constant and variable phases where the intensity is maximized; and (iii) if the phase difference is non-zero, adjusting the phase of the selected element accordingly. In some embodiments, such an experimental adjustment of the relative phases is combined with the use of a sonication model.

Measuring the total phase of the focus relative to the phase of the global focus may be accomplished by (i) driving the segment at a variable phase while driving the other segments at a constant phase, thereby varying an intensity of the global focus; (ii) determining a phase difference, if any, between the constant and variable phases where the intensity is maximized; and (iii) if the phase difference is non-zero, adjusting the total phase of the segment based thereon. Determining the phase difference may involve imaging the focus, e.g., using MR-ARFI. The total phase of the focus may be adjusted by applying phase shifts of equal magnitude to all of the transducer elements of the segment generating that focus. In some embodiments, the method further includes measuring a location of the focus associated with each segment relative to a location of the global focus, determining whether the focus is co-located with the global focus, and, if not, shifting the focus to the global focus.

In another aspect, a method, in accordance with various embodiments, for focusing an ultrasound transducer arrangement having multiple separate, independently movable segments (wherein each transducer segment again includes a plurality of transducer elements) includes driving each segment so as to generate an ultrasound focus; measuring a location of the respective focus relative to a location of a global focus; and determining whether the respective focus is co-located with the global focus and, if not, shifting it to the global focus.

Measuring the location of the focus relative to the global focus may include imaging the focus, e.g., using MR-ARFI or thermal imaging. Shifting the focus may be accomplished by physically moving the segment or, alternatively or additionally, by applying a phase gradient across the transducer elements of the segment.

In yet another aspect, various embodiments of the invention provide a system for focusing ultrasound which includes an ultrasound transducer arrangement having a plurality of separate, independently movable segments, each transducer segment including a phased array of transducer elements for generating an ultrasound focus; an MRI system for imaging the ultrasound foci associated with the segments; and a control facility in communication with the magnetic resonance imaging system and the ultrasound transducer arrangement. The control facility is configured to (i) drive each segment to generate the associated ultrasound focus, (ii) determine (based at least in part on an image of the ultrasound focus) whether the focus is co-located and in phase with a global focus, and, if the focus of an individual segment is not co-located with the global focus, (iii) adjust at least one of a position, a total phase, or a phase gradient of the segment so as to co-locate and bring the focus in phase with the global focus.

In some embodiments, the transducer segments are mechanically uncoupled. In other embodiments, the transducer segments are mechanically coupled. For example, the transducer segments may form a linkage mechanism with a single degree of freedom. The MRI system, ultrasound transducer arrangement, and control facility may be collectively configured to image the ultrasound foci by MR-ARFI.

In another aspect, the invention provides, in various embodiments, a method of treating a target using ultrasound. The method includes arranging a plurality of separate, independently movable transducer segments (each comprising a plurality of transducer elements) around the target; calibrating the arrangement of the transducer segments; and then simultaneously driving the transducer segments to focus ultrasound into the target, thereby treating the target. The transducer segments may be arranged so as to exploit acoustic windows. Calibrating the arrangement of transducer segments is accomplished by (i) driving each segment to generate an ultrasound focus, and (ii) imaging the ultrasound focus of each segment to determine whether it coincides with a global focus at the target and, if not, adjusting the segment to bring the ultrasound focus in coincidence with the global focus.

Determining whether the ultrasound focus of a particular segment coincides with the global focus may involve determining whether the ultrasound focus is co-located with the global focus and/or whether the ultrasound focus is in phase with the global focus. If the focus associated with a segment is not co-located with the global focus, a position or a phase gradient of the segment may be adjusted. If the focus associated with a segment is out of phase with the global focus, the total phase of the segment may be adjusted.

In a further aspect, certain embodiments of the invention are directed to a control system for operating an ultrasound system including an arrangement of separate, independently movable transducer segments (each transducer segment comprising a phased array of transducer elements for generating an ultrasound focus associated with the segment) used in conjunction with an MRI system. The control system includes circuitry for (i) driving each segment to generate an associated ultrasound focus, (ii) based at least in part on an image of the ultrasound focus, determining whether the focus is co-located and in phase with a global focus, and, if not, (iii) adjusting at least one of a position, a total phase, or a phase gradient of the segment so as to co-locate and bring the focus in phase with the global focus.

BRIEF DESCRIPTION OF THE DRAWINGS

The foregoing will be more readily understood from the following detailed description of the invention in conjunction with the drawings, wherein.

DETAILED DESCRIPTION

Figure 1:
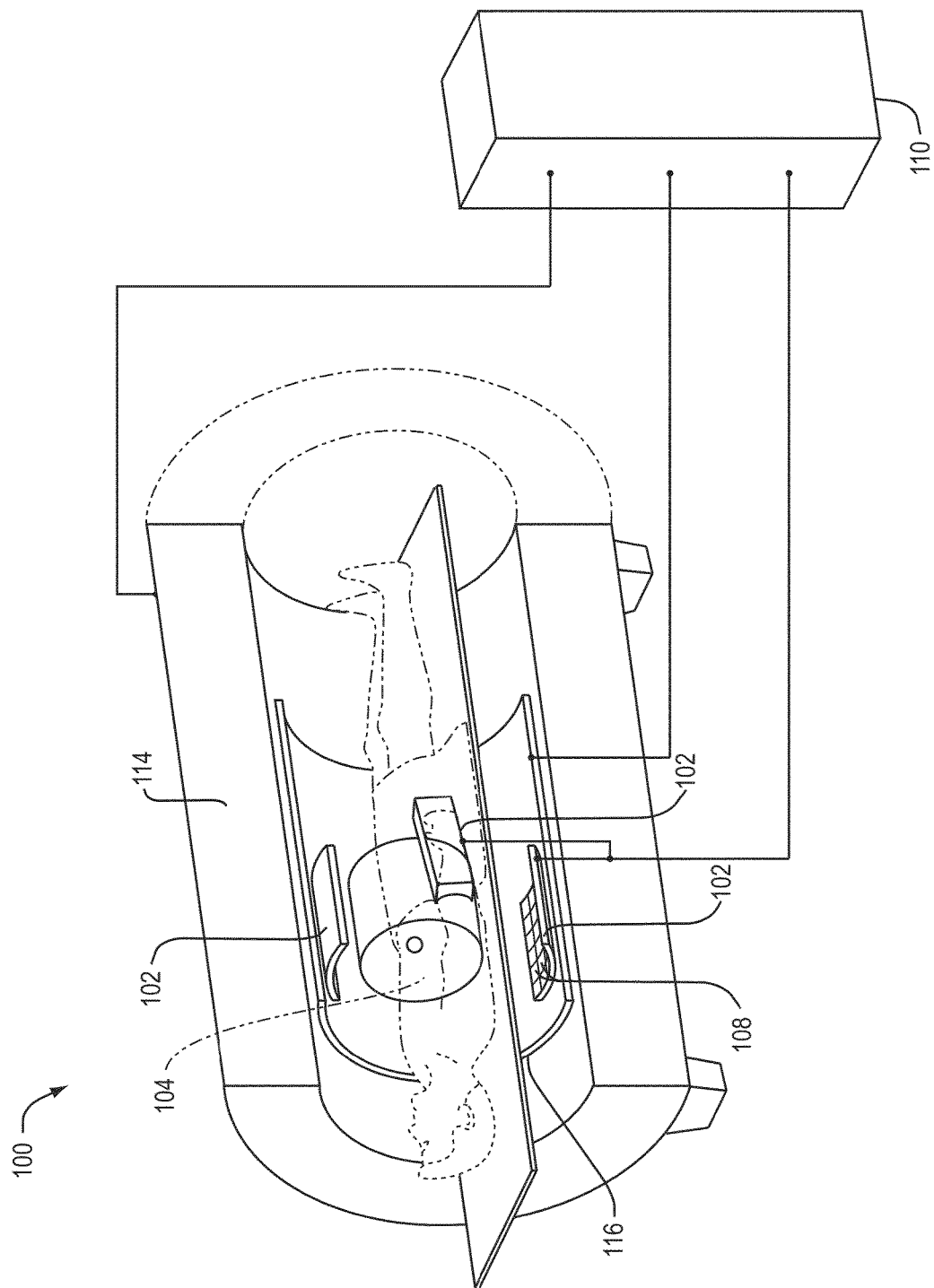
FIG. 1 is a schematic drawing illustrating an MR-guided focused ultrasound system with a multi-segment ultrasound transducer in accordance with various embodiments.

FIG. 1 illustrates schematically an exemplary magnetic-resonance-guided focused ultrasound system 100 in accordance with various embodiments of the invention. The system includes several ultrasound transducer segments 102, which are arranged around the torso 104 of a patient and directed towards a target 106 in a region of interest (ROI) inside the patient, e.g., in the patient's liver. The segments 102 may each be affixed to a corresponding housing or support structure. Alternatively, the segments 102 may be mounted on a common housing that has loosely connected movable parts which allow the segments to be translated and/or rotated with respect to one another. In some embodiments, the relative motion between each pair of transducer elements has six degrees of freedom—i.e., three rotational and three translational degrees of freedom. In other embodiments, the relative motion between at least some of the transducers is partially constrained. For example, certain transducers used for the treatment of long bones have multiple segments that form a mechanical linkage or chain. The segments may be mechanically coupled by hinges, rivets, bearings, bolted joins, shafts, rollers, universal joints, or other means that eliminate one or more translational or rotational degrees of freedom. A chain of segments connected by hinges, for instances, forms a single-degree-of-freedom linkage mechanism. Mechanical couplings between segments may be rigid or flexible. Flexible couplings can be provided for a continuum of coupling strengths (approaching rigid couplings at the strong end), and may include elastic elements such as springs. Generally, flexible couplings allow some misalignment between the links.

Each transducer segment 102 may comprise a one- or two-dimensional array (i.e., a row or a matrix) of individually controllable transducer elements 108. In other embodiments, the transducer elements 108 may be arranged in a non-coordinated fashion, i.e., they need not be spaced regularly or arranged in a regular pattern. In still other embodiments, one or more of the segments each include only one transducer element 108. The segments may have a curved (e.g., spherical or parabolic) shape, as illustrated, or may include one or more planar or otherwise shaped sections. Their dimensions may vary, depending on the application, between millimeters and tens of centimeters. The transducer elements 108 may be piezoelectric ceramic elements. Piezo-composite materials, or generally any materials capable of converting electrical energy to acoustic energy, may also be used. To damp the mechanical coupling between the elements 108, they may be mounted on the housing(s) using silicone rubber or any other suitable damping material.

The transducer elements 108 are separately controllable, i.e., they are each capable of emitting ultrasound waves at amplitudes and/or phases that are independent of the amplitudes and/or phases of the other transducers. A control facility 110 serves to drive the transducer elements 108. The control facility 110 may include separate control modules for each of the transducer segments 102. For n transducer elements 108 of a segment 102, a control module within the control facility 110 may contain n control circuits each comprising an amplifier and a phase delay circuit, each control circuit driving one of the transducer elements. The control facility 110 may split a radio frequency (RF) input signal, typically in the range from 0.1 MHz to 4 MHz, to provide n channels for the n control circuit (and additional channels for the other transducer segments). The control module may be configured to drive the individual transducer elements 108 of one segment 102 at the same frequency, but at different phases and different amplitudes so that they collectively produce a focused ultrasound beam. The control facility 110 may also include, for each of the transducer segments 102, an additional amplifier and phase delay circuit, which may be used to adjust the total amplitude and phase of the respective segment.

The control facility 110 desirably provides computational functionality, which may be implemented in software, hardware, firmware, hardwiring, or any combination thereof, to compute the required phases and amplitudes for a desired focus location. The computations carried out in the control facility may be based on sonication models for the transducer segments and/or experimental feedback about the focus quality, as described further below. In general, the control facility may include several separable apparatus, such as a frequency generator, one or more beamformers containing the amplifier and phase delay circuitry for each control module, and a computer (e.g., a general-purpose computer) performing the computations and communicating the phases and amplitudes for the individual transducer elements 108 to the beamformer(s). Such systems are readily available or can be implemented without undue experimentation.

The MRgFUS system 100 further includes an MRI apparatus 112 in communication with the control facility 110. The apparatus 112 may include a cylindrical electromagnet 114, which generates a static magnetic field within a bore thereof. During medical procedures, the patient may be placed inside the bore on a movable support table, and positioned such that an imaging region encompassing the ROI (e.g., the patient's liver) falls within a region where the magnetic field is substantially uniform. The magnetic field strength within the uniform region is typically between about 1.5 and about 3.0 Tesla. The magnetic field causes hydrogen nuclei spins to align and precess about the general direction of the magnetic field. An RF transmitter coil 116 surrounding the imaging region emits RF pulses into the imaging region, causing some of the aligned spins to oscillate between a temporary high-energy non-aligned state and the aligned state. This oscillation induces RF response signals, called the MR echo or MR response signals, in a receiver coil, which may, but need not, be the transmitter coil 116. The MR response signals are amplified, conditioned, and digitized into raw data using an image processing system, and further transformed into arrays of image data by methods known to those of ordinary skill in the art. Based on the image data, the target 106 (e.g., a tumor) is identified. Further, in some embodiments, the position and/or orientation of the segments are determined from MRI markers in the image (e.g., generated by MR coils that are embedded in or affixed to the segments). The ultrasound transducer segments 102 are then each driven so as to focus ultrasound into (or near) the treatment region.

To align the foci generated by the various transducer segments 102 with one another and with the target 106, the foci may be visualized using one of a number of magnetic-resonance-based imaging techniques, such as, e.g., thermal MRI or MR-ARFI. Because MR-ARFI generally requires lower ultrasound energies during alignment and calibration procedures than other methods, and the ultrasound intensity preceding the actual treatment should be minimized to avoid damage to tissue outside the target, MR-ARFI is typically preferred. In MR-ARFI, a transducer is driven so as to focus an ultrasound wave pulse into the body at or near the target. The ultrasound wave exerts acoustic radiation pressure onto the material along its path. At the focus, where the waves converge, this pressure is highest, resulting in a temporary local displacement of the material in the longitudinal direction and/or in shear waves that propagate radially away from the focus. Thus, the ultrasound pressure creates a displacement field that directly reflects the acoustic field. The displacement field may be visualized by applying transient-motion or displacement-sensitizing magnetic field gradients to the imaging region by gradient coils, which are part of standard MRI systems and are typically located near the cylindrical electromagnet 114. When the ultrasound pulse is applied in the presence of such gradients, the resulting displacement is directly encoded into the phase of the MR response signal. For example, the gradient coils and transducer may be configured such that the ultrasound pulse pushes material near the focus towards regions of the magnetic field with higher field strengths. In response to the resulting change in the magnetic field, the phase of the MR response signal changes proportionally, thereby encoding in the signal the displacement caused by the ultrasound radiation pressure.

Figure 2A:
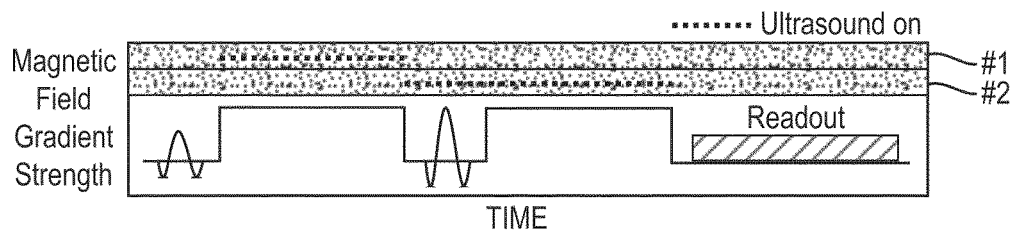
FIGS. 2A-2C illustrate several MR-ARFI sequences in accordance with various embodiments.
Figure 2B:
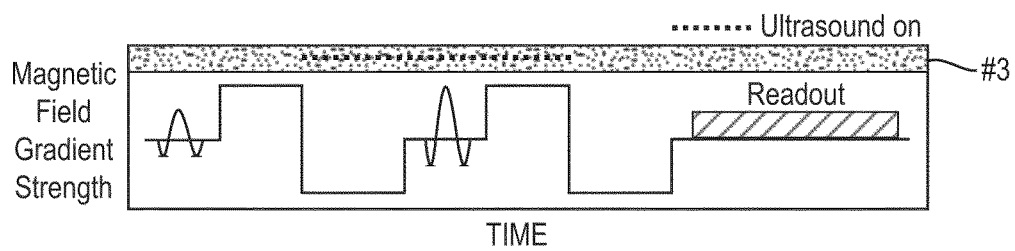
Figure 2C:
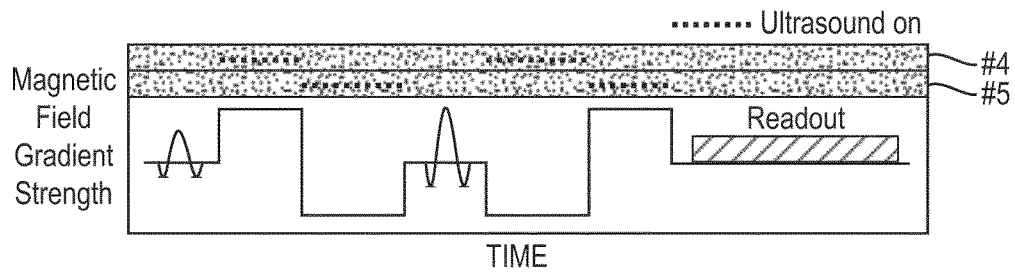

To achieve high image contrast, the ultrasound pulse, encoding gradients, and RF pulse are precisely timed with respect to each other according to a suitable displacement-encoding sequence. FIGS. 2A-2C illustrate five exemplary MR-ARFI sequences that may be used in embodiments of the invention. These sequence diagrams illustrate the order in which the displacement-encoding magnetic field gradients (thin solid lines), ultrasound pulses (dotted lines), and RF pulses (thick solid lines) appear in time. Three different field gradient sets are shown: two single lobes (a), repeated bipolars (b), and inverted bipolars (c). For gradient set (a), ultrasound may be applied during either the first or the second lobe. Similarly, for gradient set (c), ultrasound may be applied during the first or the second halves of the bipolars. In general, MR-ARFI sequences utilize magnetic field gradients that are synchronized with the ultrasound pulses. In preferred embodiments, a sequence like the repeated bipolar sequence (b) shown in FIG. 2B may be used. The imaging sequence may be programmed into the control facility 110. The control facility 110 may then send trigger signals to the ultrasound transducer modules and the MRI hardware to ensure correct timing between the signals.

Figure 3A:
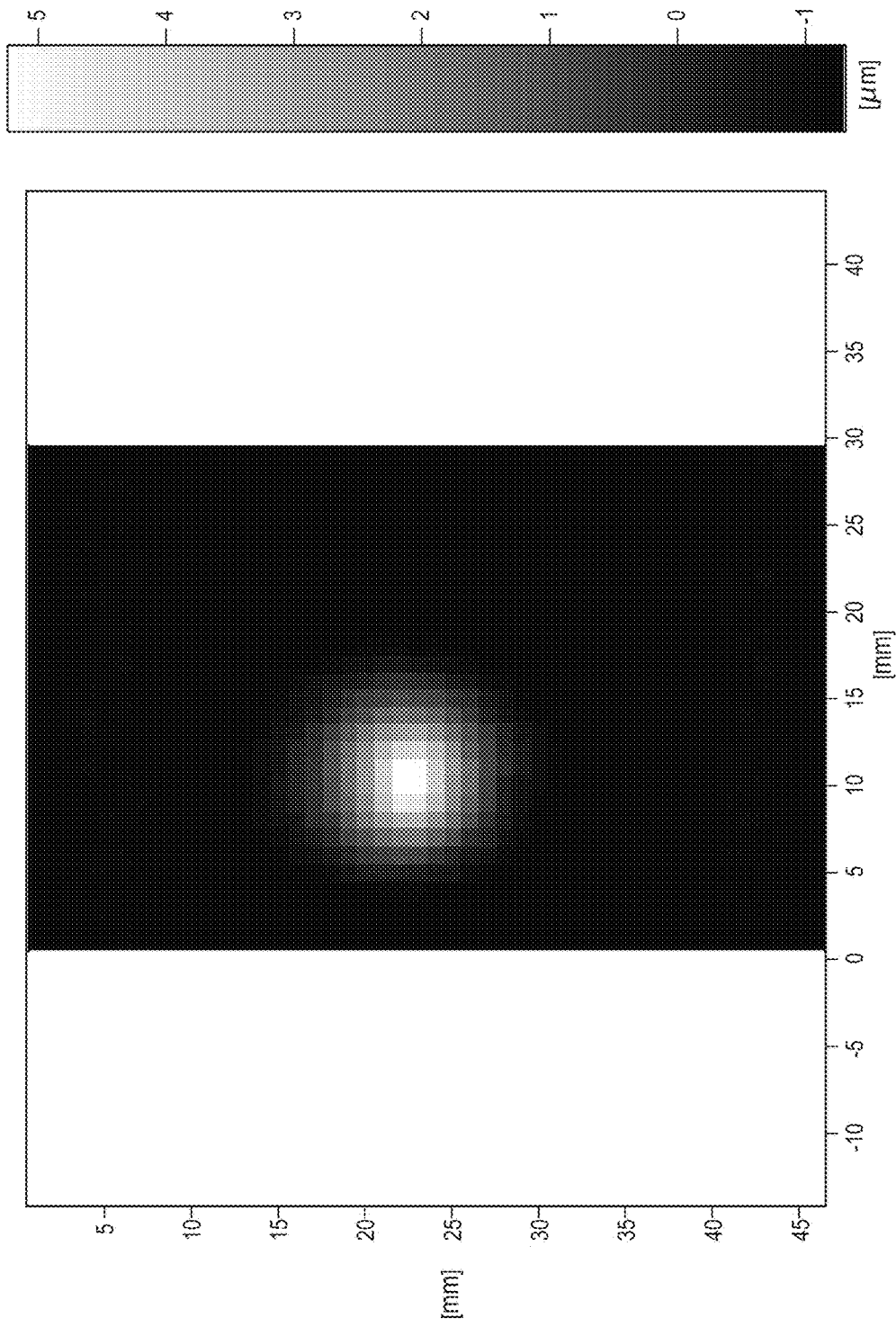
FIG. 3A is an image of material displacements in an ultrasound focus region in accordance with some embodiments.
Figure 3B:
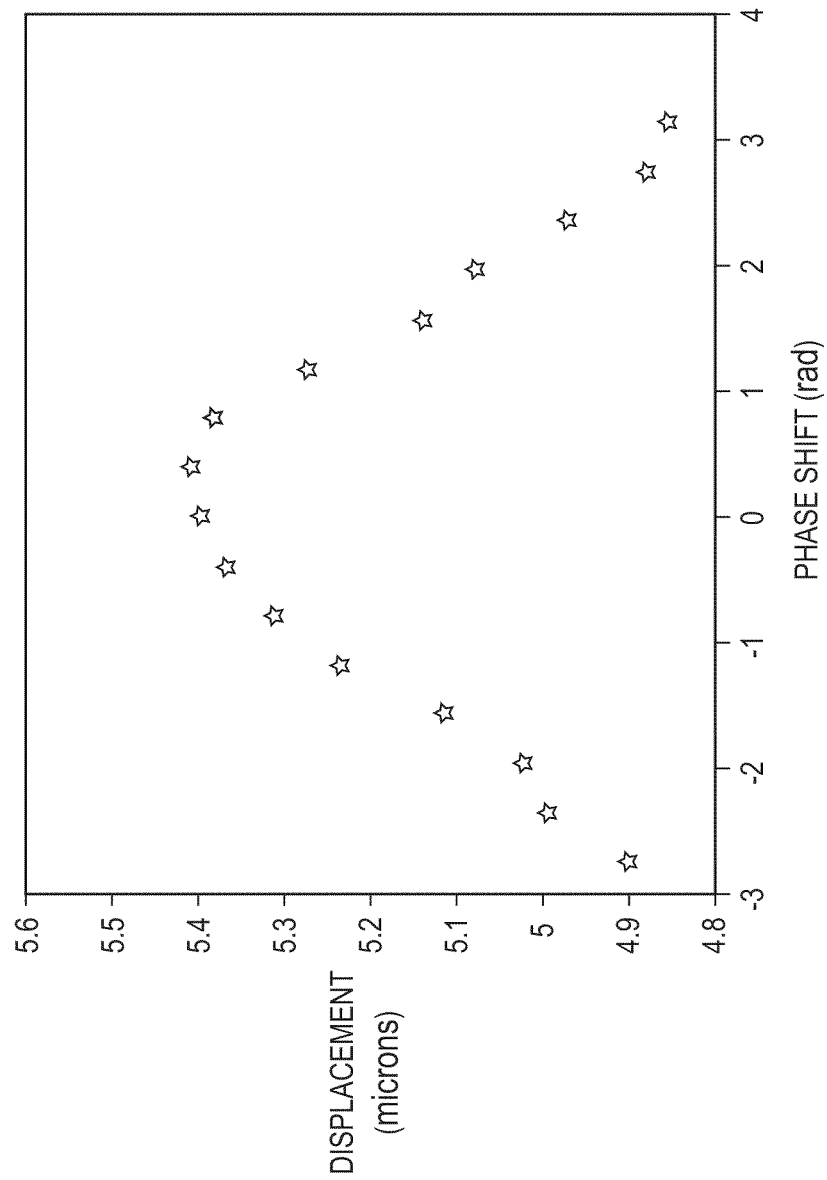
FIG. 3B is a graph illustrating material displacement in the focus center as a function of the phase of an individual transducer element, as it may be used in calibrations methods in accordance with various embodiments.

An example of an MR-ARFI image of an ultrasound focus region is shown in FIG. 3A. As shown, the material displacement with respect to an equilibrium position varies between about −1 μm and 5 μm. In general, the stronger the acoustic field intensity, the greater will be the maximum displacement at the center of the focus. The acoustic field intensity, in turn, is maximized when the individually controlled portions of the transducer (i.e., the elements within a transducer segments and/or the various segments) emit acoustic waves that are all in phase at the focus position. If a transducer element is out of phase with respect to the others, the focus intensity in the center decreases. This relationship can be exploited to optimize the focus, and thus to map and adjust the transducer elements and/or segments, as detailed further below. Assuming, for example, that all but one of the transducer elements of a segment are properly configured, the correct phase of the last element can be determined by tuning the phase over a full cycle (e.g., between −π and +π), measuring for each phase the displacement in the focus center, and then setting the phase to the value corresponding to the maximum displacement. FIG. 3B depicts the results of such an adjustment procedure. In the illustrated example, the material displacement over the full phase cycle of one element varies between about 4.85 μm and about 5.4 μm. The maximum displacement occurs at about 0.12 rad. Consequently, the focus intensity and quality can be improved by introducing a phase shift of 0.12 rad for the tested transducer element.

In principle, it is possible to adjust the focus of a multi-segment transducer by adjusting each individual transducer element 108, without regard to the arrangement of the elements 108 in multiple segments 102. In practice, however, this procedure may take an undesirably long time, and may not be necessary. Since the transducer elements 108 within one segment are rigidly connected with each other, a-priori knowledge of the surface of that transducer segment may suffice to create a focus of sufficient quality with that segment. Such a-priori knowledge may be obtained in a calibration procedure outside the body, e.g., using a phantom. Suitable calibration procedures are described, for example, in U.S. Provisional Patent Application No. 61/251,450, filed Oct. 14, 2009, the entire disclosure of which is hereby incorporated herein by reference.

In brief, mapping of the full transducer array of a segment may be accomplished by varying and adjusting the phase of each element, one at a time, while driving the remaining elements at constant phase, and monitoring the focus quality, e.g., using MR-ARFI. Typically, after each element has been mapped independently, the focus quality has significantly improved. Since the necessary phase adjustments of the transducer elements are all interrelated, however, the focus may not yet be optimal after one iteration. Therefore, in some embodiments, the procedure may be repeated iteratively. With each iteration, the phase adjustments made to maximize the displacement in the focus will, generally, decrease. Thus, a termination condition may be defined by setting a threshold value for phase adjustments, below which further adjustments are deemed immaterial or not clinically necessary. The number of iterations required to reach the termination condition may depend on the order in which the transducer elements are mapped. A mathematical algorithm, for example a "greedy algorithm" as known to persons of skill in the art, may be used to select a mapping order that results in fast convergence of the phase settings.

When a transducer segment calibrated with a phantom is placed into a treatment setup (such as the one shown in FIG. 1), the ultrasound beam may experience aberration due to its passage through tissue that differs from the phantom material. While such aberration may be significant for bones, it is typically less significant, or even negligible, for soft tissues, such as the breast, liver, or prostate. Utilizing a transducer comprising multiple independently movable segments facilitates, in many applications, arrangements in which the beam paths only go through soft tissues. Thus, to achieve the desired global focus, the foci produced by the various segments often need only be properly aligned and phase-adjusted.

In some embodiments, fine adjustments to the relative phases (and, in some cases, amplitudes) between transducer elements of a pre-calibrated transducer segment are desired after integration of the segment into the treatment setup. Further, in certain embodiments, the individual transducer segments are mapped directly in the treatment setup. In both cases, phase adjustments may be based on geometric and/or material parameters of a sonication model (including, e.g., information about the relative arrangement of the segment and target, and/or acoustic material parameters of the tissue(s) between the segment and target), iterative experimental feedback, or a combination of both. For example, transducer elements within a segment may be grouped according to a-priori knowledge about the types and acoustic properties of tissues along the respective acoustic wave paths to the target, and the relative phases between groups of elements may then be adjusted using MR-ARFI. Experimental feedback may also be used to ascertain an unknown parameter of a sonciation model. Further detail about the calculation of relative phases (and, optionally, amplitudes) based on a sonication model is described, for example, in U.S. patent application Ser. No. 12/425,698, filed on Apr. 17, 2009, and further detail about the combination of sonication-model-based computations and measurements of focus quality to efficiently adjust the relative phases of the transducer elements is described in a U.S. patent application entitled, "Efficient Ultrasound Focusing," filed on even date herewith. Both applications are hereby incorporated herein by reference in their entireties.

A-priori knowledge of the tissues may be obtained, for example, from measurements of the acoustic material properties of the tissues. Information about the location and/or orientation of the segment relative to the target may be known from the design of the treatment setup, and/or measured with sensors, such as MR tracking coils or position sensors (e.g., tilt indicators, ultrasound encoders, or optical encoders) embedded in the segment. Further, if multiple segments are mechanically linked, information about the location and/or orientation of one segment may provide information about the location and/or orientation of another segment. For example, the position of one segment of a linkage mechanism, together with the relative orientations of the joints between the segments, suffices to determine the positions of the other transducer segments, reducing the number of sensors needed.

Figure 4:
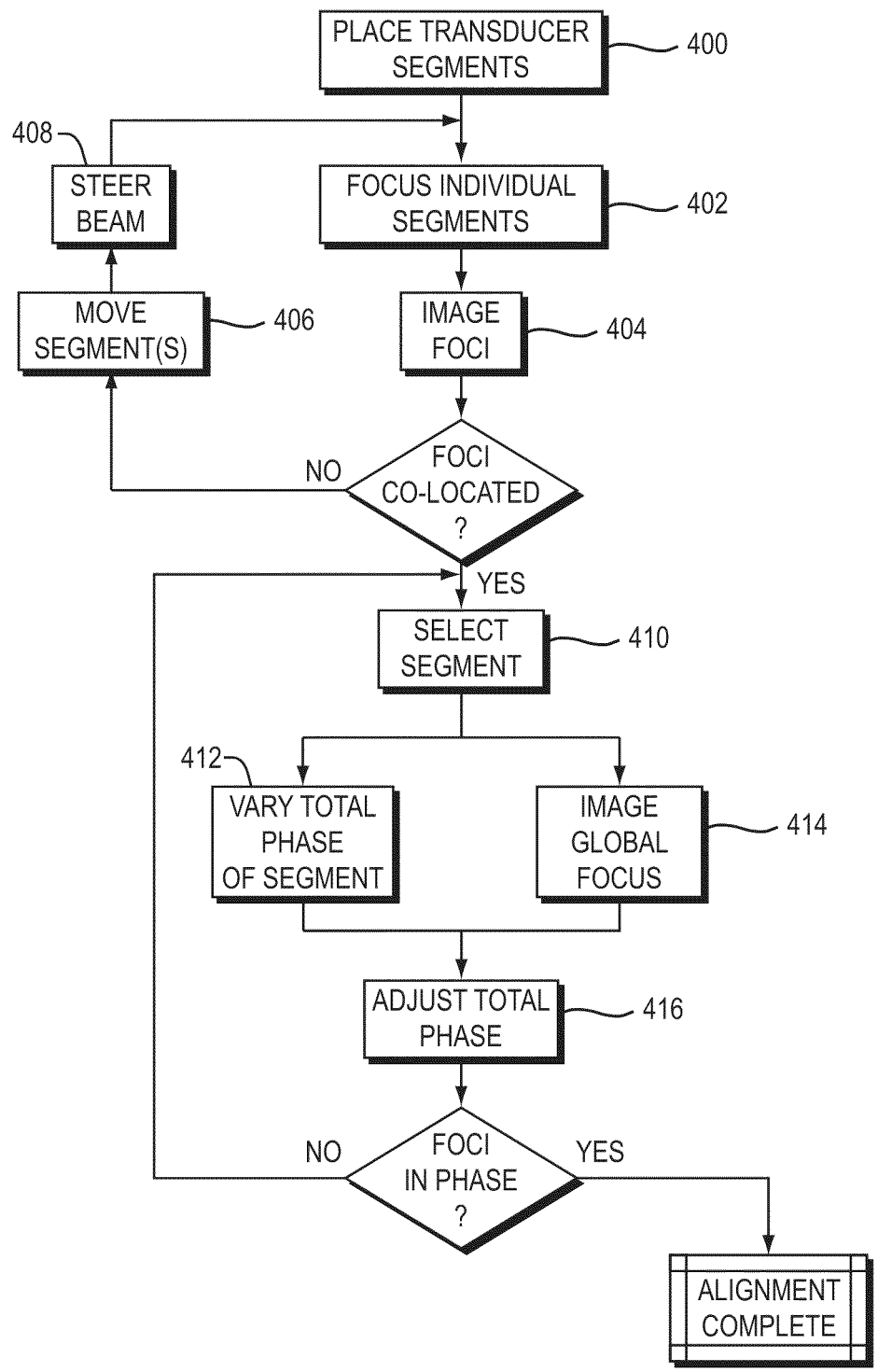
FIG. 4 is a flow chart illustrating a method of focusing a multi-segment ultrasound transducer array in accordance with various embodiments of the invention.

FIG. 4 illustrates an exemplary method for focusing a multi-segment transducer in accordance with various embodiments. In a first step 400, the transducer segments (which may have been calibrated outside the treatment setup) are placed around a target, typically inside an imaging apparatus. The locations of the various segments may be chosen to exploit acoustic windows, e.g., such that absorption or scattering of ultrasound between the segments and the target is minimized. Each segment is then driven to produce an ultrasound focus, and any adjustments to the transducer elements that may be desirable to improve the quality or correct the location of each individual focus is made (step 402). Then, two or more segments are driven simultaneously, and the resulting ultrasound foci are imaged (step 404), e.g., using MR-ARFI, to determine whether they are co-located. If a focus of one of the segments is displaced from the other foci (and/or the target), that segment is physically moved, or the steering of its beam is electronically adjusted, to correct for the displacement. Typically, physical translation of the transducer segment is used first to bring the focus approximately in the right location (step 406), and fine-tuning of the location is subsequently accomplished by adjusting the relative phases of the transducer elements (step 408). For example, to translate the beam laterally while maintaining the focus quality, a linear phase-gradient shift may be applied to the transducer array. The segments may generally be aligned in any order. For example, two foci may first be brought to overlap, then a third focus generated by a third segment may be added and aligned with the other two, and so on. Alternatively, a reference focus may be chosen, and each of the other foci may be co-located with the reference focus individually. The foci may also be generated simultaneously at the outside, and iteratively be aligned with each other.

Once the foci are co-located in a global focus, their total phases are adjusted so that the waves from different transducer segments arrive in phase at a center point or region of the focus. The initial total phases of the transducers may (but need not) be based on information about the relative positions and/or orientations of the transducer segments (which may be available, in particular, for mechanically coupled segments). When all the foci are in phase with each other, the global focus will have an intensity profile in which the intensity decreases monotonously with the distance from a center. Otherwise, when some of the foci are out of phase, a different intensity profile may be observed. For example, assuming that each segment contributes the same amount of energy to the focal region, if half of the segments are phase-shifted by $\pi$ with respect to the other half, the waves interfere destructively at the center, but form interference fringes (e.g., a ring pattern) in the surrounding region. For the purpose of bringing the ultrasound foci in phase, one transducer segment may be selected (step 410), and the total phase of that segment may be varied (step 412) while the phases of the other segments are held constant. Simultaneously with the phase variation, the global focus may be imaged (step 414), again using MR-ARFI, for example. The intensity at the center of the global focus (and thus, in MR-ARFI, the tissue displacement) will be maximized when the ultrasound wave of the segment under test is in phase with the overall ultrasound field generated by the other segments. Therefore, the total phase of the tested segment at which the intensity is maximized constitutes the phase shift by which the total phase is subsequently adjusted (step 416). The adjustment step is repeated for each transducer segment until all the segments produce ultrasound foci that are in phase with each other. Alternatively, the phase shifts may first be determined for all the segments without adjustments being made, and subsequently, all the phase adjustments may be made at once. Once the transducer arrangement has been calibrated, i.e., the individual foci have been co-located in brought in phase, the transducer segments may be driven simultaneously to treat the target.

Although the present invention has been described with reference to specific details, it is not intended that such details should be regarded as limitations upon the scope of the invention, except as and to the extent that they are included in the accompanying claims.

What is claimed is:

1. A method of focusing an ultrasound transducer arrangement comprising a plurality of separate, spaced-apart, independently movable segments, each transducer segment comprising a plurality of individually controllable transducer elements and each transducer element comprising a plurality of piezoelectric elements, the method comprising:
   (a) for each of the plurality of transducer segments, adjusting relative phases of the transducer elements within the segment so as to create a focus associated with the segment; and
   (b) following step (a), bringing the foci associated with the segments in phase by measuring, for each segment, a total phase associated with the focus relative to a phase of a global focus; and
   (c) determining whether the focus is in phase with the global focus and, if not, adjusting the total phase of the focus to a phase of the global focus.

2. The method of claim 1 wherein measuring the total phase of the focus relative to the phase of the global focus comprises (i) driving the segment at a variable total phase while driving the other segments at a constant total phase, thereby varying an intensity of the global focus; (ii) determining a phase difference, if any, between the constant and variable total phases where the intensity is maximized; and (iii) if the phase difference is non-zero, adjusting the total phase of the segment based thereon.

3. The method of claim 2 wherein determining the phase difference comprises imaging the focus.

4. The method of claim 3 wherein imaging the focus is accomplished using magnetic-resonance acoustic radiation force imaging.

5. The method of claim 1 wherein adjusting the total phase of the focus comprises applying phase shifts of equal magnitude to all of the transducer elements of the segment generating the focus.

6. The method of claim 1 further comprising measuring a location of the focus relative to a location of the global focus, determining whether the focus is co-located with the global focus, and, if not, shifting the focus to the global focus.

7. A method of focusing an ultrasound transducer arrangement comprising a plurality of separate, spaced-apart, independently movable segments, each transducer segment comprising a plurality of individually controllable transducer elements and each transducer element comprising a plurality of piezoelectric elements, the method comprising:
   (a) for each of the plurality of transducer segments, adjusting relative phases of the transducer elements within the segment so as to create a focus associated with the segment; and
   (b) following step (a), bringing the foci associated with the segments to overlap by measuring, for each segment, a location of the focus relative to a location of a global focus; and
   (c) determining whether the focus is co-located with the global focus and, if not, shifting the focus to the global focus.

8. The method of claim 7 wherein measuring the location of the focus relative to the global focus comprises imaging the focus.

9. The method of claim 8 wherein imaging the focus is accomplished using thermal imaging.

10. The method of claim 7 wherein shifting the focus comprises physically moving the segment.

11. The method of claim 7 wherein shifting the focus comprises applying a phase gradient across the transducer elements of the segment.

12. A system for focusing ultrasound, the system comprising:
   an ultrasound transducer arrangement comprising a plurality of separate, spaced-apart, independently movable segments, each transducer segment comprising a phased array of individually controllable transducer elements and each transducer element comprising a plurality of piezoelectric elements for generating an ultrasound focus associated therewith;
   a magnetic resonance imaging system for imaging the ultrasound foci associated with the segments; and
   in communication with the magnetic resonance imaging system and the ultrasound transducer arrangement, a control facility configured to, for each segment, (i) adjust relative phases of the transducer elements within the segment so as to create a focus associated with the segment, (ii) following step (i), based at least in part on an image of the ultrasound focus, determine whether the focus is co-located and in phase with a global focus, and, if not, (iii) adjust at least one of a position, a total phase, or a phase gradient of the segment so as to co-locate and bring the focus in phase with the global focus.

13. The system of claim 12 wherein the transducer segments are mechanically uncoupled.

14. The system of claim 12 wherein the transducer segments are mechanically coupled.

15. The system of claim 14 wherein the transducer segments form a linkage mechanism with a single degree of freedom.

16. The system of claim 12 wherein the magnetic resonance imaging system, ultrasound transducer arrangement, and control facility are collectively configured to image the ultrasound foci using magnetic-resonance acoustic radiation force imaging.

17. A method of treating a target using ultrasound, the method comprising:
   arranging a plurality of separate, spaced-apart independently movable transducer segments, each comprising a plurality of individually controllable transducer elements and each transducer element comprising a plurality of piezoelectric elements, around the target;
   calibrating the arrangement of the transducer segments by (i) adjusting relative phases of the transducer elements within each segment so as to generate an ultrasound focus associated with the segment, (ii) following step (i), imaging the ultrasound focus of each segment to determine whether it coincides with a global focus at the target and, if not, (iii) adjusting the segment to bring the ultrasound focus in coincidence with the global focus; and
   simultaneously driving the transducer segments to focus ultrasound into the target, thereby treating the target.

18. The method of claim 17 wherein determining whether the ultrasound focus coincides with the global focus comprises determining whether the ultrasound focus is co-located with the global focus.

19. The method of claim 17 wherein determining whether the ultrasound focus coincides with the global focus comprises determining whether the ultrasound focus is in phase with the global focus.

20. A control system for operating an ultrasound system used in conjunction with a magnetic resonance imaging system, the ultrasound system comprising an arrangement of separate, spaced-apart, independently movable transducer segments, each transducer segment comprising a phased array of individually controllable transducer elements and each transducer element comprising a plurality of piezoelectric elements, for generating an ultrasound focus associated therewith, the control system comprising circuitry for (i) adjusting relative phases of the transducer elements within each segment to generate an associated ultrasound focus, (ii) following step (i), based at least in part on an image of the ultrasound focus, determining whether the focus is collocated and in phase with a global focus, and, if not, (iii) adjusting at least one of a position, a total phase, or a phase gradient of the segment so as to co-locate and bring the focus in phase with the global focus.

* * * * *